(12) United States Patent
Lee et al.

(10) Patent No.: US 9,658,605 B2
(45) Date of Patent: May 23, 2017

(54) SURGICAL ROBOT AND CONTROL METHOD THEREOF

(71) Applicant: SAMSUNG ELECTRONICS CO., LTD., Suwon-si, Gyeonggi-do (KR)

(72) Inventors: Kwang Kyu Lee, Yongin-si (KR); Woong Kwon, Seongnam-si (KR); Kyung Shik Roh, Seongnam-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 793 days.

(21) Appl. No.: 13/723,688

(22) Filed: Dec. 21, 2012

(65) Prior Publication Data

US 2013/0116706 A1    May 9, 2013

(30) Foreign Application Priority Data

Dec. 23, 2011 (KR) .................. 10-2011-0140778

(51) Int. Cl.
*A61B 19/00* (2006.01)
*G05B 6/00* (2006.01)
(Continued)

(52) U.S. Cl.
CPC .............. *G05B 6/00* (2013.01); *A61B 34/30* (2016.02); *A61B 34/37* (2016.02); *A61B 34/76* (2016.02)

(58) Field of Classification Search
CPC ......... G05B 2219/40517; B25J 9/1648; A61B 19/2203; A61B 34/30; A61B 34/37; A61B 34/76
See application file for complete search history.

(56) References Cited

U.S. PATENT DOCUMENTS 7,108,688 B2    9/2006  Jensen
2001/0013764 A1   8/2001  Blumenkranz et al.
(Continued)

FOREIGN PATENT DOCUMENTS

EP    2113449 A2    11/2009
JP    H05111889 A    5/1993
(Continued)

OTHER PUBLICATIONS

Panadda Marayong, Motion Control Methods for Human-Machine Cooperative Systems, Dissertation submitted to The Johns Hopkins University for the degree of Doctor of Philosophy. Aug. 2007, available at https://jscholarship.library.jhu.edu/bitstream/handle/1774.2/32564/thesis-pmarayong-small.pdf.*

(Continued)

*Primary Examiner* — Gary Jackson
*Assistant Examiner* — Scott T Luan
(74) *Attorney, Agent, or Firm* — Harness, Dickey & Pierce, PLC

(57) ABSTRACT

A method for controlling a surgical robot includes calculating an external force acting on a robot arm mounted with a surgical instrument, filtering the external force acting on the robot arm when a central point of an incision is set, calculating a virtual force to enable the surgical instrument which is positioned away from the central point of the incision to return to the central point of the incision, and applying the calculated virtual force to the filtered external force, to control movement of the robot arm. As a result, it is possible to compactly design the surgical robot and thereby reduce the volume of the surgical robot.

10 Claims, 5 Drawing Sheets

(51) Int. Cl.
  *A61B 34/30*     (2016.01)
  *A61B 34/37*     (2016.01)
  *A61B 34/00*     (2016.01)

(56) References Cited

U.S. PATENT DOCUMENTS

2008/0314181 A1   12/2008   Schena
2009/0240259 A1    9/2009   Nelson et al.

FOREIGN PATENT DOCUMENTS

JP      2005329476 A     12/2005
JP      2011-156407       8/2011

OTHER PUBLICATIONS

"Under, Over and Critical Damping", OCW 18.03SC, MIT OpenCourseWare.*
"Motion Control Methods for Human-Machine Cooperative Systems", Panadda Marayoung, Aug. 2007, Chapter 2, pp. 19-53.
Japanese Office Action dated Oct. 4, 2016 issued in corresponding Japanese Application No. 2012-280326 (with translation).

* cited by examiner

SURGICAL ROBOT AND CONTROL METHOD THEREOF

CROSS-REFERENCE TO RELATED APPLICATIONS

This application claims the priority benefit of Korean Patent Application No. 10-2011-0140778, filed on Dec. 23, 2011 in the Korean Intellectual Property Office, the disclosures of which are incorporated herein by reference.

BACKGROUND

1. Field

Embodiments disclosed herein relate to a surgical robot used for minimally invasive surgery and a method for controlling the same.

2. Description of the Related Art

Minimally invasive surgery generally refers to surgery capable of minimizing the size of an affected area when an incision is made in the body to perform an operation. A representative example of minimally invasive surgery includes laparoscopic surgery which may involve operations in the pelvic or abdominal regions, for example. Minimally invasive surgery may involve using a surgical robot. Minimally invasive surgery may be performed while observing an image, after a plurality of small holes (incisions or invasive holes) having a size of 0.5 cm to 1.5 cm are drilled in the abdomen, and a video camera and a variety of apparatuses are inserted through the incisions. This type of surgery is unlike laparotomy in which a large incision is made in, for example, abdomen.

Minimally invasive surgery has advantages of little pain after surgery, fast recovery of intestinal motion, early food ingestion, short hospitalization period, short recovery time, and excellent cosmetic effects due to narrow incision size, as compared to laparotomy. Due to these advantages, minimally invasive surgery is used for cholecystectomy, prostatic carcinoma surgery, hernia repair and the like and applications thereof continue to grow.

A surgical robot includes a master robot to transmit a necessary signal generated by operation of a user and a slave robot to receive the signal from the master robot and directly perform operations required for surgery. The master robot and the slave robot may be integratedly or separately disposed in an operating room.

The slave robot includes a robot arm for surgical operations and surgical instruments are mounted on the front end of the robot arm. When surgery is performed using surgical instruments mounted on the front end of the robot arm, the surgical instruments move along with the movement of the robot arm.

Minimally invasive surgery using a surgical robot includes a manual positioning mode in which a user (an operator, generally a doctor or other qualified medical professional) holds and moves the robot arm on which surgical instruments are mounted such that the surgical instruments are inserted through incisions and are positioned in a surgery site, and a teleoperation mode in which a user remotely manipulates surgical instruments using a master robot. In the two modes, it is necessary to control movement of robot arms (or surgical instruments) to a limited level in order to prevent surgical instruments mounted on the robot arm from intruding into the incisions. When the limited movement of surgical instruments is not satisfied, extension of incisions or incidental bleeding of diseased parts occurs, thus causing damage to the skin or internal body parts.

Accordingly, surgical instruments mounted on the front end of the robot arm control the robot arm such that surgical instruments pivot about a virtual pivot central point set at a predetermined position. Such a virtual point is referred to as remote center of motion (RCM).

The positions of incisions are fixed via translational and rotational movement of surgical instruments and the link structure of the robot arm is designed as a parallelogrammic structure (four-link structure) in order to secure this point as the RCM. Since each link of the four-link structure necessarily passes one point regardless of movement or configuration, it is possible to realize a RCM without additional operation in both manual positioning mode and teleoperation mode.

The methods for realizing a RCM of the robot arm are broadly divided into passive type and active type. The passive type is a method in which the RCM of a robot arm is realized using a mechanical structure, while the active type is a method in which the RCM of a robot arm is realized using a control algorithm.

A method for realizing RCM using the aforementioned four-link structure by using a passive type method has a problem in that the volume of the surgical robot supporting the robot arm is increased. Also, when a surgical robot system is configured with a plurality of surgical robots, the system occupies a large area due to increased total volume, thus disadvantageously causing a narrow workspace, and there is further an increased risk of collision between surgical robots during a surgical operation.

SUMMARY

Therefore, it is one aspect of the present invention to provide a surgical robot and a method for controlling the same in which the surgical robot is compactly designed and the volume of the surgical robot is reduced by realizing a RCM of a robot arm, using an active-type control algorithm, rather than a passive-type mechanical structure.

Also, it is another aspect of the present invention to provide a surgical robot and a method for controlling the same in which the surgical robot (or surgical robot system) is compactly designed in an active-type RCM realization manner to impart applicability of general-purpose serial-type robot of the related art to a surgical robot field.

Also, it is another aspect of the present invention to provide a surgical robot and a method for controlling the same in which a limited movement of robot arms (or surgical instruments) is secured in order to prevent surgical instruments mounted on a robot arm from intruding into incisions in a manual positioning mode in which a user (an operator, generally a doctor or a qualified medical professional) holds and moves the robot arm on which the surgical instruments are mounted such that the surgical instruments are inserted through the incisions and are positioned in a surgery site.

Additional aspects of the invention will be set forth in part in the description which follows and, in part, will be obvious from the description, or may be learned by practice of the invention.

In accordance with one aspect of the present invention, provided is a method for controlling a surgical robot including: calculating an external force acting on a robot arm mounted with a surgical instrument; filtering the external force acting on the robot arm, when a central point of an incision is set; calculating a virtual force, enabling the surgical instrument which is positioned away from or deviated away from the central point (Pc) of the incision to return to the central point of the incision; and adding or applying the calculated virtual force to the filtered external force to control movement of the robot arm.

The control of movement of the robot arm may be carried out in a manual positioning mode in which a user directly holds and moves the robot arm mounted with a surgical instrument by hand such that the surgical instrument is inserted through the incision and is positioned in a surgery site.

The calculation of the external force acting on the robot arm may include: detecting torque information acting on respective pivot joints constituting the joint part using a force/torque sensor; and subtracting torque information of pivot joints required for maintenance of present position or movement of the robot arm in the absence of an external force, which may be calculated in accordance with the following Equation 1, from the detected torque information, to calculate torque information of pivot joints generated by an external force actually applied from the outside to the robot arm.

$$\sigma_{calculated}=M(q)\ddot{q}+c(q,\dot{q})\dot{q}+g(q) \qquad \text{[Equation 1]}$$

wherein q is a pivot angle of a pivot joint, M is an inertia matrix, c is Coriolis force and a centrifugal force, and g is gravity.

The filtering of the external force acting on the robot arm may be carried out by removing torque information, rendering the remote center of motion present on the surgical instrument to be deviated from the central point of the incision, from torque information of the pivot joint generated by external force applied to the robot arm from the outside.

The calculation of the virtual force may include: mounting or setting a virtual spring and a virtual damper between the central point of the incision and the remote center of motion; calculating a deviation between the central point of the incision and the remote center of motion; and calculating the virtual force using the calculated deviation, stiffness of the virtual spring and a coefficient of the virtual damper.

In accordance with another aspect of the present invention, provided is a surgical robot including: a force/torque sensor to detect torque information acting on respective pivot joints constituting a joint part associated with an operation of the surgical robot; and a control unit to filter the external force acting on the robot arm, when a central point of an incision is set, to calculate an virtual force, enabling the surgical instrument which is positioned away from or deviated away from the central point (Pc) of the incision to return to the central point of the incision; and to add or apply the calculated virtual force to the filtered external force to thereby control movement of the robot arm.

The control unit may control movement of the robot arm in a manual positioning mode in which a user directly holds and moves the robot arm mounted with the surgical instrument, by hand, such that the surgical instrument is inserted through the incision and is positioned in a surgery site.

The control unit may receive torque information acting on pivot joints constituting the joint part associated with the operation of the surgical robot, and subtract torque information of pivot joints required for maintenance of present position or movement of the robot arm from the detected torque information in the absence of an external force, which may be calculated in accordance with the following Equation 1, to calculate torque information of pivot joints generated by an external force actually applied from the outside to the robot arm.

$$\tau_{calculated}=M(q)\ddot{q}+c(q,\dot{q})\dot{q}+g(q) \qquad \text{[Equation 1]}$$

wherein q is a pivot angle of a pivot joint, M is an inertia matrix, c is Coriolis force and a centrifugal force, and g is gravity.

The control unit may remove torque information, rendering the remote center of motion present on the surgical instrument to be deviated from the central point of the incision, from torque information of the pivot joint generated by external force applied to the robot arm from the outside, to filter an external force acting on the robot arm.

The control unit may mount or set a virtual spring and a virtual damper between the central point of the incision and the remote center of motion, calculate a deviation between the central point of the incision and the remote center of motion, and calculate the virtual force using the calculated deviation, stiffness of the virtual spring and coefficient of the virtual damper, to calculate the virtual force.

In accordance with another aspect of the present invention, a surgical robot may include a sensor to measure a force directly applied by a user to a robot arm of the surgical robot and a control unit to filter an external force directly applied to the robot arm after a central point of an incision is set, to calculate a virtual force to enable the surgical instrument which deviates away from the central point of the incision to return to the central point of the incision, and to apply the calculated virtual force to the filtered external force to control movement of the robot arm.

The control unit may receive first torque information measured by the sensor corresponding to the force directly applied by the user to the robot, calculate second torque information of pivot joints of the robot arm required for maintenance of a present position or movement of the robot arm without the direct force being applied by the user, and obtain third torque information corresponding to the external force directly applied to the robot, by subtracting the second torque information from the first torque information.

The control unit may calculate the virtual force by calculating a deviation between the central point of the incision and a remote center of motion. The control unit may continuously update a position of the remote center of motion until receiving an indication manual positioning of the robot is completed.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Hereinafter, embodiments of the present invention will be described with reference to the accompanying drawings.

Figure 1:
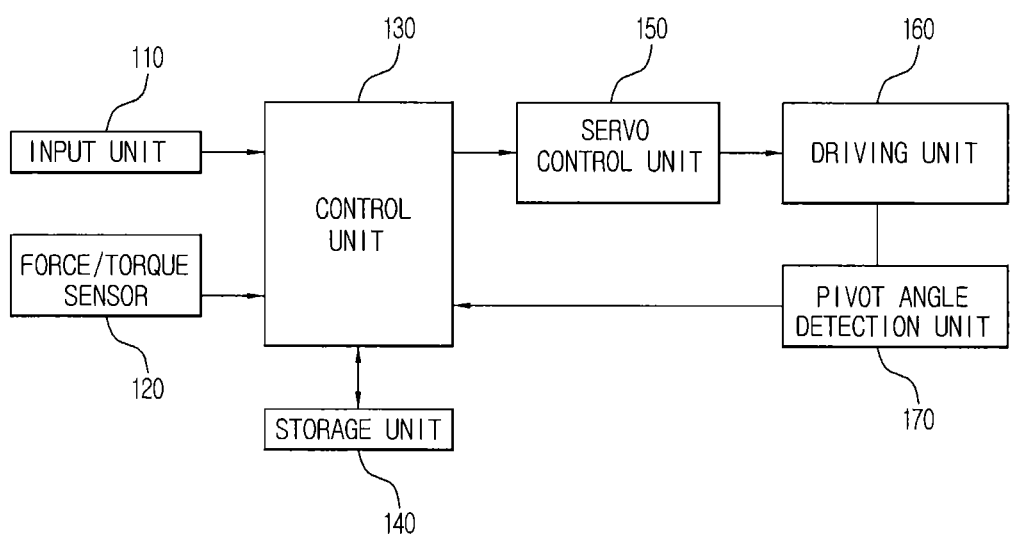
FIG. 1 is a block diagram illustrating a controlled configuration of a surgical robot according to one embodiment of the present invention.

FIG. 1 is a block diagram illustrating a controlled configuration of a surgical robot according to one embodiment of the present invention.

As shown in FIG. 1, the surgical robot according to one embodiment of the present invention includes an input unit 110, a force/torque sensor 120, a control unit 130, a storage unit 140, a servo control unit 150, a driving unit 160 and a pivot angle detection unit 170. Here, it is noted some or all components shown in FIG. 1 may be integrated together, or may be separately disposed.

The input unit 110 enables a user (operator) to input an operation command (e.g., work command) of a surgical robot and includes a user interface (UI) or remote operator or the like. Also, the input unit 110 may include an apparatus or device such as keyboard, pedal or footswitch, joystick, or mouse to enable an operator to set the position of a central point (Pc in FIG. 2) of incisions. The input unit 110 may further have additional features to assist the user in operating the surgical robot, including haptic feedback capability, head-mounted displays, or virtual reality devices, for example. The input unit 110 may be remotely located from the robot arm and surgical robot such that a user may input an operation command from a remote station. Communication between the input unit 110, control unit 130, storage unit, servo control unit 150, and/or driving unit 160 may be performed over a wired or wireless network, for example.

The force/torque sensor 120 may be mounted on the joint (e.g., a shoulder joint, elbow joint and/or wrist joint) associated with an operation (e.g., movement, work, etc.) of the surgical robot, to detect forces and moments (torques) acting on respective pivot joints constituting the joint. The force/torque sensor 120 may include a 6-axis force-torque sensor to detect translational forces in three directions (Fx, Fy and Fz) and rotational moments in three directions (Mx, My and Mz), for example.

The control unit 130 may include a controller to control the overall operation of the surgical robot. The control unit 130 calculates an external force that acts on the robot arm on which a surgical instrument 210 is mounted, filters an external force that acts on the robot arm when a central point (Pc) of incisions is set, calculates a virtual force enabling the surgical instrument 210 which may be positioned away from the central point (Pc) of the incision to return to the central point (Pc) and adds the calculated virtual force to the filtered external force to control movement of the robot arm.

The storage unit 140 may include a memory that stores advance information that helps the surgical robot to control a limited movement of the robot arm (or surgical instruments) and information generated during the limited movement control in a manual positioning mode. The storage unit 140 may further store computer-aided design (CAD) information of the robot arm and the surgical instrument 210 adhered to the robot arm, and position and direction information of the central point (Pc) of incisions that are obtained using forward kinematics in the process of setting the central point of incisions. The storage unit may further be embodied as a non-transitory computer readable medium, including hard disks, floppy disks, flash memory or memory cards (e.g., a USB drive), or optical media such as CD ROM discs and DVDs.

Although a configuration in which the storage unit 140 to store advance information required for limited movement control of the robot arm and information generated during limited movement control is separately provided has been described in embodiments of the present invention, advance information required for limited movement control may be stored in an inner memory of the control unit 130 without configuration of the storage unit 140.

The servo control unit 150 calculates a torque control signal corresponding to a target joint torque ($\tau_d$) transferred from the control unit 130 to a driving unit 160 to rotate respective pivot joints of joint part associated with the operation of the surgical robot.

The driving unit 160 is an actuator such as a motor, to transfer power such as electricity or hydraulic force to respective pivot joints constituting a joint part, which rotates respective pivot joints of the joint part associated with operations of the surgical robot according to a torque control signal transferred from the servo control unit 150. There may be more than one joint part associated with operations of the surgical robot.

The pivot angle detection unit 170 detects a pivot angle of the actuator (driving unit) to rotate respective pivot joints of a joint part associated with operations of the surgical robot. The pivot angle detection unit 170 may include an encoder, for example. Accelerometers, gyroscopes, and the like may also be used to measure changes in the pivot joints of a joint part.

Figure 2:
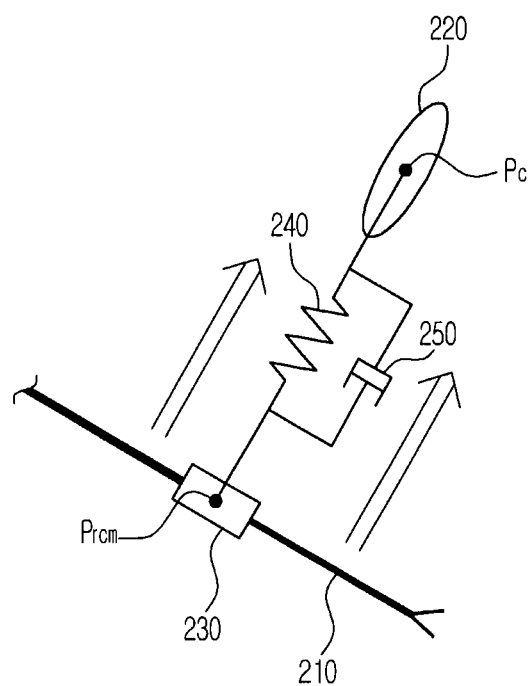
FIG. 2 is a view illustrating a method for controlling movement of robot arm during a manual positioning mode realized in a surgical robot according to one embodiment of the present invention.

FIG. 2 is a view illustrating a method for controlling movement of a robot arm during a manual positioning mode realized in a surgical robot according to one embodiment of the present invention.

The present invention discloses a method for controlling movement of the robot arm in order to prevent the surgical instrument 210 mounted on a robot arm from intruding into the incision 220 in a manual positioning mode in which a user (operator) directly holds and moves the robot arm on which the surgical instrument 210 is mounted such that the surgical instrument 210 is inserted through the incision 220 and is positioned in a surgery site. Here, it is noted that the robot arm and surgical instrument may be positioned in a surgery site as needed to perform the desired operation. For example, the robot arm and surgical instrument may be portable, may be fixed, or may be detachably disposed to a site (e.g., the railing of an operating table, or other object).

First, the user holds and moves the robot arm (not shown) to which the surgical instrument 210 is attached by hand, such that the end of the surgical instrument 210 is positioned in the central point (Pc) of the incision and the longitudinal direction of the surgical instrument 210 is positioned substantially perpendicularly to the surface of the incision 220. Next, the user manipulates the input unit 110 (e.g., a pedal or mouse) to set the present position of the surgical instrument 210 to the central point of the incision (during manipulation of the input unit). The set central point (Pc) of the incision is positioned away from the surgical robot (robot arm) and should be equivalent to a remote center of motion (Prcm) of the surgical instrument 210 adhered to the robot arm, regardless of movement of the robot arm.

The end of the surgical instrument 210 adhered to the robot arm is positioned at the central point (Pc) of the incision and the longitudinal direction of the surgical instrument 210 is positioned substantially perpendicular to the surface of the incision 220.

Before the central point (Pc) of the incision is set in the manual positioning mode, the power applied to the robot arm by the user is detected through the force/torque sensor 120 mounted on the joint and movement of the robot arm is controlled using the detected information (e.g., level and direction of force). That is, the user freely holds and moves the robot arm and there is no necessity of limiting movement of the robot arm until the central point (Pc) of the incision is set. However, once the position of the central point (Pc)

of the incision is set, a force enabling deviation of the present position of the central point (Pc) of the incision is filtered from the force applied to the robot arm by the user. Also, as shown in FIG. 2, a virtual slider 230 is mounted to the surgical instrument 210, and a virtual spring 240 and a virtual damper 250 are mounted between the set central point (Pc) of the incision and the virtual slider 230 on the surgical instrument 210. A virtual restoration force (the virtual restoration force acts in an arrow direction as shown in FIG. 2) is calculated, which enables the surgical instrument 210 deviated from the central point (Pc) of the incision to be returned to the position of the central point (Pc) of the incision. By applying the calculated virtual restoration force to the filtered user force (external force) and moving the robot arm, based on the virtual restoration force-applied filtered external force, it is possible to make the remote center of motion (Prcm) on the surgical instrument 210 adhered to the robot arm pass through the central point (Pc) of the incision.

A method for controlling the surgical robot according to one embodiment of the present invention will be described based on FIG. 3 and with reference to FIGS. 4 and 5 below.

As an initial condition to describe the operation of embodiments of the present invention, CAD information of a robot arm and the surgical instrument 210 adhered to the robot arm may be previously stored as advance information that helps the surgical robot to control a limited movement of the robot arm (or surgical instruments) in the storage unit 140.

When the operation command of the surgical robot is input from the user through the input unit 110, a manual positioning mode in which the surgical instrument 210 is inserted through the incision 220 and is positioned to a surgery site begins.

When the manual positioning mode begins, the control unit 130 receives force/torque information acting on respective pivot joints constituting the joint part from the force/torque sensor 120 and calculates an external force acting on the robot arm using input force/torque information (310).

Here, the calculation of external force refers to the calculation of a force/torque acting on the joint by the user or surroundings other than torque required for maintenance of the present position or movement of the surgical robot (more specifically, robot arm).

The robot arm coupled to the force/torque sensor 120 and the surgical instrument 210 coupled to the robot arm respectively have an inherent mass arm. Accordingly, the force/torque sensor 120 detects pure external force generated externally as well as internal indirect force/torque information generated due to the weight of the robot arm and the surgical instrument 210 coupled thereto. Also, unlike a case in which the surgical robot moves slowly, fast movement of the surgical robot causes generation of an inertial force. Accordingly, internal indirect force/torque information transferred to the force/torque sensor 120 may include information of force/torque based on inertial force.

That is, while the surgical robot performs work, the force/torque sensor 120 detects force/torque information of pure external force as well as indirect force/torque information of inertia generated by the mass and by movement of the robot arm and surgical instrument 210. Accordingly, indirect force/torque information of inertia generated by the mass by and movement of the robot arm and the surgical instrument 210 may be calculated. A value obtained by subtracting indirect force/torque information obtained from force/torque information from the indirect force/torque information detected in the force/torque sensor 120 is regarded as force/torque information generated by pure external force and movement of the robot arm should be controlled based on this force/torque information. That is, the pure external force applied from an outside source may be obtained by subtracting from the force/torque information sensed by the force/torque sensor 120 the calculated indirect force/torque information.

The control unit 130 models the robot arm from CAD information (CAD data) of the robot arm and the surgical instrument 210 adhered thereto and calculates torque information required for maintenance of a present position or movement of the robot arm. That is, the control unit 130 calculates torque information ($\tau_{calculated}$) of pivot joints required for maintenance of a present position or movement in the absence of external force using the following Equation 1.

$$\tau_{calculated} = M(q)\ddot{q} + c(q,\dot{q})\dot{q} + g(q) \quad \text{[Equation 1]}$$

wherein q is a pivot angle of a pivot joint, M is an inertia matrix, c is Coriolis force and a centrifugal force, and g is gravity.

The value obtained by subtracting torque information ($\tau_{calculated}$) of pivot joints required for maintenance of the present position or present movement from torque information ($\tau_{measured}$) acting on pivot joints detected using the force/torque sensor 120 corresponds to torque information of pivot joint ($\tau_{external}$) of an external force actually applied from the outside to the robot arm and satisfies a relationship represented by the following Equation 2.

$$\tau_{external} = \tau_{measured} - \tau_{calculated} \quad \text{[Equation 2]}$$

The user moves the surgical instrument 210 adhered to the robot arm to a desired position by directly applying external force to the robot arm by hand. Then, the user positions the end of the surgical instrument 210 adhered to the robot arm at the central point (Pc) of the incision and the longitudinal direction of the surgical instrument 210 is positioned substantially perpendicular to the surface of the incision 220. The present (when the input unit is manipulated) position of the end of the surgical instrument 210 (which may be positioned away from the central point of the incision) is set to the central point of the present incision by manipulating the input unit 110 (using e.g., a keyboard, pedal or mouse).

At this time, the control unit 130 determines the position and direction of the end of surgical instrument 210 using forward kinematics, and the determined position and direction of the end of surgical instrument 210 are regarded as the position and direction of the central point (Pc) of the incision and are stored in the storage unit 140.

Information associated with the incision 220 stored in the storage unit 140 will be described with reference to FIG. 4.

The central point Pc is positioned on the surface of the incision 220 and represents a three-dimensional central point of incision 220.

C1 and C2 independently represent three-dimensional vectors and are basis vectors which are orthonormal to each other and transverse the surface of the incision 220.

Prcm is a remote center of motion present on the surgical instrument 210, which refers to the intersection between the surface of the incision 220 and the surgical instrument 210. When the input unit 110 such as keyboard, pedal or mouse is manipulated (e.g., to set the central point of incision), Prcm may be identical to Pc (Prcm=Pc).

Po is an endpoint of the surgical instrument 210, and Po, Prcm and Pc may be identical (Po=Prcm=Pc), when the input unit 110 such as a keyboard, pedal or mouse is manipulated (e.g. to set the central point of incision). When an incision is made and the surgical instrument 210 is inserted into the patient, for example, Po may be positioned away from the remote center of motion Prcm and central point of incision Pc, as shown in FIG. 5.

Pi represents a point at which the surgical instrument 210 is connected to the robot arm, or a limited point at which the surgical instrument 210 may intrude into the incision 220.

Figure 3:
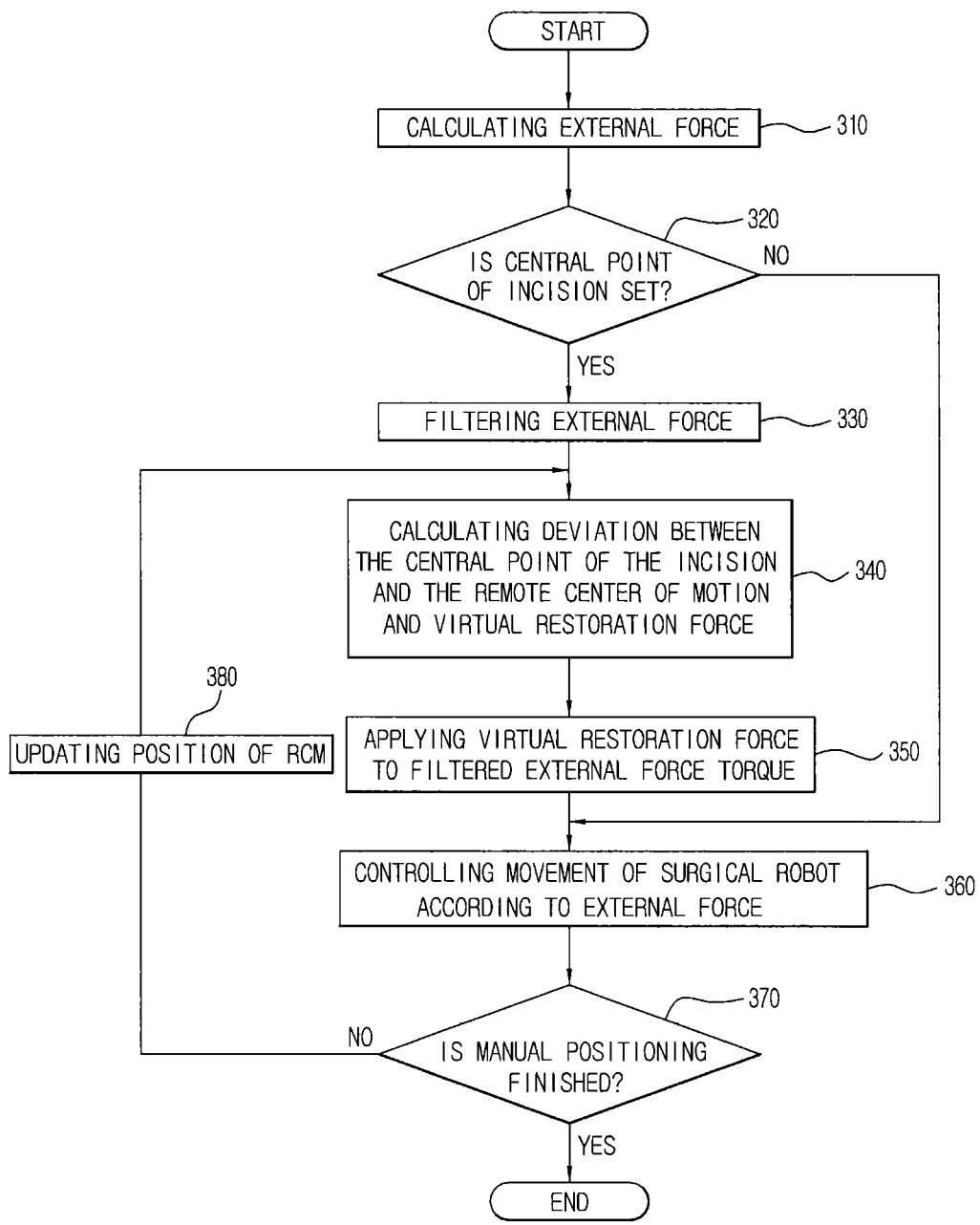
FIG. 3 is a flowchart illustrating a method for controlling a surgical robot according to one embodiment of the present invention.
Figure 4:
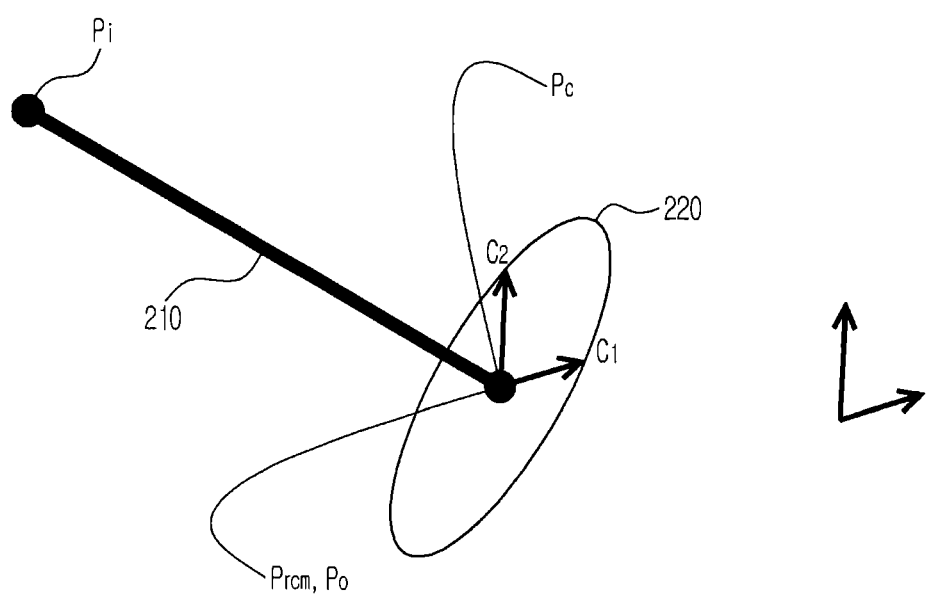
FIG. 4 is a view illustrating a method for setting a central point of the incision shown in FIG. 3.

Regarding operation 320 of FIG. 3, the control unit 130 determines whether the central point (Pc) of the incision is set (320).

When the central point (Pc) of the incision is determined to be not set yet ("No" in 320), the control unit 130 controls movement of the surgical robot (robot arm) according to an external force (360). The control unit 130 adds an external force actually applied from the outside to the robot arm, obtained in accordance with Equation 2, to gravity torque information ($\tau_{g(q)}$) required for maintenance of present conditions of the robot arm to obtain a target joint torque ($\tau_d$) and outputs the same to the servo control unit 150. If necessary, torque information ($\tau_{calculated}$) obtained in accordance with Equation 1 may be subjected to low pass filtering. The target joint torque ($\tau_d$) may be represented by the following Equation 3:

$$\tau_d = \tau_g(q) + \alpha \cdot \tau_{external} \qquad \text{[Equation 3]}$$

wherein $\alpha$ is a positive constant, which may be stored in the storage unit.

Also, a damping term as shown in the following Equation 4 may be added in order to prevent excessive movement of the robot arm.

$$\tau_d = \tau_g(q) + \alpha \cdot \tau_{external} - b \cdot \dot{q} \qquad \text{[Equation 4]}$$

wherein b is a damping coefficient and a positive scalar, which may be stored in the storage unit.

Regarding the operation 320 of FIG. 3, when the central point (Pc) of the incision is determined to be set ("YES" in 320), the control unit 130 filters external force (330).

The filtering of external force refers to the removal of torque that contributes to an increase of deviation between the central point (Pc) of the incision and the remote center of motion (Prcm) based on torque information of the pivot joint ($\tau_{external}$) of an external force actually applied from the outside to the robot arm, obtained in accordance with Equation 2.

Figure 5:
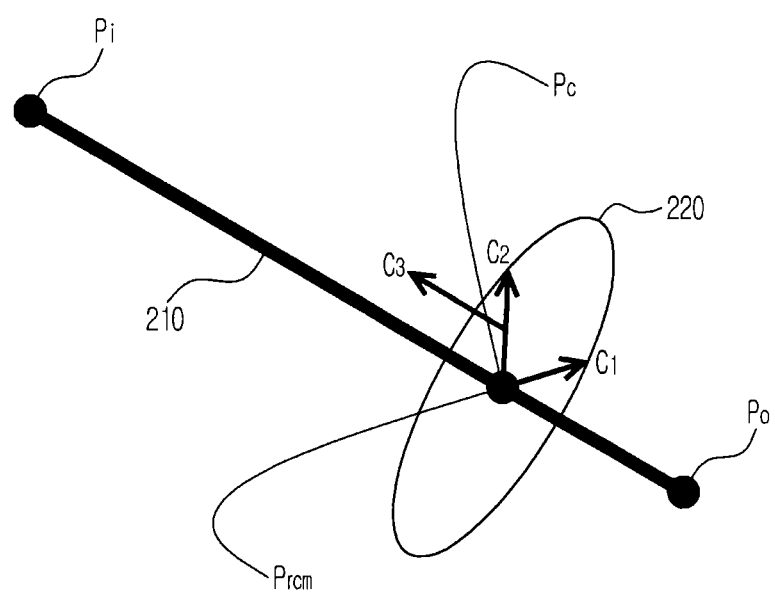
FIG. 5 is a view illustrating a method of filtering an external force shown in FIG. 3.

For filtering of external force, first, the control unit 130 calculates lambda ($\lambda$) in accordance with the following Equation 5:

$$\lambda = \frac{c_3^T(P_{rcm} - P_i)}{c_3^T(P_o - P_i)} \qquad \text{[Equation 5]}$$

wherein C3 is an orthonormal vector of basis vectors C1 and C2 that transverse the surface of the incision 220 (see FIG. 5).

Next, the control unit 130 calculates a Jacobian matrix (Jrcm) in the remote center of motion (Prcm) using the following Equation 6:

$$J_{rcm} = J_i + \lambda(J_o - J_i) \qquad \text{[Equation 6]}$$

Next, the control unit 130 calculates a constraint Jacobian matrix (Jc) in accordance with the following Equation 7.

$$J_C = [c_1 c_2]^T J_{rcm} \qquad \text{[Equation 7]}$$

Next, the control unit 130 calculates a filtered external force torque ($\tau_{external,filtered}$) in accordance with the following Equation 8:

$$\tau_{external,filtered} = (I - J_C^\# J_C) \tau_{external} \qquad \text{[Equation 8]}$$

wherein I is an identity matrix and the filtered external force torque ($\tau_{external,filtered}$) is a torque in which a torque component that renders the remote center of motion (Prcm) to be deviated from the central point (Pc) of the incision (e.g., a torque component shifting the remote center of motion in directions C1 and C2) is removed from the external force torque ($\tau_{external}$) obtained by Equation 2. That is, the multiplication factor (I−Jc#Jc) represents a filtering amount that may reduce a value of the external force torque calculated from Equation 2.

Referring to FIG. 3 again, after the external force is filtered, the control unit 130 calculates a deviation between the central point ($P_c$) of the incision and the remote center of motion (Prcm) and a virtual restoration force (340).

First, the control unit 130 calculates a deviation ($e_{rcm}$) between the central point (Pc) of the incision and the remote center of motion (Prcm) in accordance with Equation 9:

$$e_{rcm} = [c_1 c_2]^T (P_{rcm} - P_c) \qquad \text{[Equation 9]}$$

Next, the control unit 130 calculates a virtual restoration force ($\tau_c$) which enables the surgical instrument 210 deviated from the central point ($P_c$) of the incision to return to the position of the central point ($P_c$) of the incision in accordance with the following Equation 10:

$$\tau_c = K \cdot e_{rpm} + D \cdot \dot{e}_{rpm} \qquad \text{[Equation 10]}$$

wherein K is a stiffness of virtual spring 240 and D is a coefficient of the virtual damper 250 for stabilization. Values for K and D may be stored in the storage unit.

After the virtual restoration force ($\tau_c$) is calculated, the control unit 130 applies the calculated virtual restoration force ($\tau_c$) to the filtered external force torque ($\tau_{external,filtered}$) (350).

Next, the control unit 130 controls movement of the surgical robot (robot arm) according to the external force (360). Here, the control unit 130 may apply a filtered external force torque ($\tau_{external,filtered}$), instead of the external force torque ($\tau_{external}$) used in Equation 4 for calculating the target joint torque ($\tau_d$) which uses an unfiltered external force, and adds virtual restoration force ($\tau_c$). Thus, a filtered external force ($\tau_{external,filtered}$) may be applied to Equation 4 to calculate a target joint torque ($\tau_d$) in the manual positioning mode having a limited movement control condition (incision restrictive condition) of the robot arm, and outputs the same to the servo control unit 150. The target joint torque ($\tau_d$) after the central point ($P_c$) of the incision is set may be represented by the following Equation 11:

$$\tau_d = \tau_g(q) + \alpha \cdot \tau_{external,filtered} + \tau_c - b \cdot \dot{q} \qquad \text{[Equation 11]}$$

Next, the control unit 130 determines whether manual positioning is completed (370). The control unit 130 determines that manual positioning is completed when a manual positioning completion signal is input through the input unit 110 from the user.

Unless manual positioning is completed ("NO" in 370), the control unit 130 renders the robot arm to limitedly move while updating the position of the remote center of motion (Prcm) in accordance with the following Equation 12 (380), returns to operation 340 and continuously calculates a virtual restoration force which enables the surgical instrument 210 deviated from the central point (Pc) of the incision to return to the position of the central point (Pc) of the incision:

$$P_{rcm} = P_i + \lambda(P_o - P_i) \qquad \text{[Equation 12]}$$

Meanwhile, when manual positioning is completed ("YES" in 370), the control unit 130 finishes the manual positioning mode of the surgical robot.

According to the controlled surgical robot and a method for controlling the same, it is possible to compactly design the surgical robot and thus reduce the volume of surgical robot by realizing RCM of a robot arm, using an active-type control algorithm, rather than a passive-type mechanical structure.

Also, according to the controlled surgical robot and a method for controlling the same, it is possible to impart applicability of general-purpose serial-type robot of the related art to a surgical robot field by compactly designing the surgical robot (or surgical robot system) in an active-type RCM realization manner.

While the disclosure herein has provided example embodiments of a surgical robot and control method to control the surgical robot, for example, in a medical setting to perform an operation on a patient (e.g., a human or animal or other lifeform), the disclosure is not so limited. For example, the surgical robot may be used in other settings which may benefit from the surgical robot disclosed herein. For example, the surgical robot may be utilized to perform operations in any confined space or enclosure in which an operator may need to perform controlled movements using an instrument attached to a robot arm, so as to avoid or to prevent injuries to bodies or objects, that may be located or disposed within the space or enclosure, due to imprecise movements of the surgical robot. Possible settings may include, for example, mining operations, surveillance operations, inspection operations, repair operations, bomb disposal operations, etc., however again, the disclosure is not so limited.

The apparatus and methods for controlling a configuration of the surgical robot according to the above-described example embodiments may use one or more processors, which may include a microprocessor, central processing unit (CPU), digital signal processor (DSP), or application-specific integrated circuit (ASIC), as well as portions or combinations of these and other processing devices.

The terms "module", and "unit," as used herein, may refer to, but are not limited to, a software or hardware component or device, such as a Field Programmable Gate Array (FPGA) or Application Specific Integrated Circuit (ASIC), which performs certain tasks. A module or unit may be configured to reside on an addressable storage medium and configured to execute on one or more processors. Thus, a module or unit may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules/units may be combined into fewer components and modules/units or further separated into additional components and modules.

The methods for controlling a configuration of the surgical robot according to the above-described example embodiments may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described embodiments, or vice versa. Some or all of the operations performed in the methods for controlling a configuration of the surgical robot according to the above-described example embodiments may be performed over a wired or wireless network.

Each block of the flowchart illustrations may represent a unit, module, segment, or portion of code, which comprises one or more executable instructions for implementing the specified logical function(s). It should also be noted that in some alternative implementations, the functions noted in the blocks may occur out of the order. For example, two blocks shown in succession may in fact be executed substantially concurrently or the blocks may sometimes be executed in the reverse order, depending upon the functionality involved.

Although a few example embodiments of the present invention have been shown and described, it would be appreciated by those skilled in the art that changes may be made to these embodiments without departing from the principles and spirit of the invention, the scope of which is defined in the claims and their equivalents.

What is claimed is:

1. A method for controlling a surgical robot comprising:
   calculating an external force acting on a robot arm mounted with a surgical instrument, based on an actual external force acting on the robot arm, the actual external force being a constant force over time;
   filtering the calculated external force acting on the robot arm to calculate a filtered external force, when a central point of an incision is set, the filtering of the calculated external force acting on the robot arm including removing a deviation force from the calculated external force, the deviation force being a force enabling deviation of a remote center of motion of the surgical instrument from the central point of the incision;
   calculating a virtual force independently of the filtered external force, the virtual force being a force enabling the remote center of motion of the surgical instrument deviating from the central point of the incision to return to the central point of the incision;
   applying the calculated virtual force to the calculated filtered external force to control movement of the robot arm; and
   subsequent to controlling movement of the arm,
      updating a position of the remote center of motion,
      recalculating the virtual force independently of the filtered external force, based on the updated remote center of motion, such that the filtered external force is unchanged, and
      applying the recalculated virtual force to the unchanged filtered external force to subsequently control movement of the robot arm;
   wherein the calculating of the virtual force includes,
      setting a virtual spring and a virtual damper between the central point of the incision and the remote center of motion;
      calculating a deviation between the central point of the incision and the remote center of motion; and calculating the virtual force using the calculated deviation, stiffness of the virtual spring and a coefficient of the virtual damper.

2. The method according to claim 1, wherein the control of movement of the robot arm is carried out in a manual positioning mode in which a user directly holds and moves the robot arm mounted with the surgical instrument by hand such that the surgical instrument is inserted through the incision and is positioned in a surgery site.

3. The method according to claim 1, wherein the calculation of the external force acting on the robot arm comprises:
   detecting torque information acting on respective pivot joints constituting a joint part using a force/torque sensor; and
   subtracting torque information of pivot joints corresponding to a torque value required for maintenance of a present position or movement of the robot arm without the external force being applied, from the detected torque information, to calculate torque information of pivot joints generated by the external force externally applied to the robot arm.

4. The method according to claim 3, wherein the filtering of the external force acting on the robot arm is carried out by removing torque information contributing to a deviation of the remote center of motion present on the surgical instrument from the central point of the incision, from torque information of the pivot joint generated by the external force externally applied to the robot arm.

5. The method of claim 1, wherein applying the calculated virtual force to the filtered external force to control movement of the robot arm comprises: calculating a target joint torque, based on both the filtered external force and the calculated virtual force; and outputting the target joint torque to a servo control unit coupled to the robot arm.

6. A surgical robot comprising:
   a control unit configured to,
      calculate an external force acting on a robot arm associated with an operation of the surgical robot, based on an actual external force acting on the robot arm, the actual external force being a constant force over time,
      filter the calculated external force acting on the robot arm to calculate a filtered external force, when a central point of an incision is set, the filtering of the calculated external force acting on the robot arm including removing a deviation force from the calculated external force, the deviation force being a force enabling deviation of the surgical instrument from the central point of the incision,
      calculate a virtual force independently of the filtered external force, the virtual force being a force enabling a remote center of motion present on an instrument coupled to the robot arm which deviates away from the central point of the incision to return to the central point of the incision,
      apply the calculated virtual force to the filtered external force to control movement of the robot arm, and
      subsequent to controlling movement of the robot arm, update a position of the remote center of motion,
         recalculate the virtual force independently of the filtered external force, based on the updated remote center of motion, such that the filtered external force is unchanged, and
         apply the recalculated virtual force to the unchanged filtered external force to subsequently control movement of the robot arm;
   wherein, to calculate the virtual force, the control unit is configured to,
      set a virtual spring and a virtual damper between the central point of the incision and the remote center of motion,
      calculate a deviation between the central point of the incision and the remote center of motion, and
      calculate the virtual force using the calculated deviation, stiffness of the virtual spring and a coefficient of the virtual damper.

7. The surgical robot according to claim 6, wherein the control unit is configured to control movement of the robot arm in a manual positioning mode in which a user directly holds and moves the robot arm to which the instrument is coupled, by hand, such that the instrument is inserted through the incision and is positioned in a surgery site.

8. The surgical robot according to claim 7, wherein the control unit is configured to,
   receive torque information acting on at least one pivot joint constituting a joint part of the robot arm, and
   subtract torque information of at least one pivot joint corresponding to a torque value required for maintenance of a present position or movement of the robot arm without an external force being applied, from the received torque information, to calculate torque information of at least one pivot joint generated by an external force externally applied to the robot arm.

9. The surgical robot according to claim 8, wherein, to filter the external force acting on the robot arm, the control unit is configured to remove torque information contributing to a deviation of the remote center of motion present on the instrument from the central point of the incision, from torque information of at least one pivot joint generated by the external force externally applied to the robot arm.

10. The surgical robot of claim 6, wherein applying the calculated virtual force to the filtered external force to control movement of the robot arm comprises: calculating a target joint torque, based on both the filtered external force and the calculated virtual force; and outputting the target joint torque to a servo control unit coupled to the robot arm.

* * * * *